United States Patent [19]
Rhyne et al.

[11] Patent Number: 6,050,947
[45] Date of Patent: Apr. 18, 2000

[54] METHOD AND APPARATUS FOR HARMONIC TISSUE IMAGING AND CONTRAST IMAGING USING CODED TRANSMISSION

[75] Inventors: Theodore L. Rhyne, Whitefish Bay, Wis.; Richard Y. Chiao, Clifton Park, N.Y.

[73] Assignee: General Electric Company, Milwaukee, Wis.

[21] Appl. No.: 09/224,650

[22] Filed: Dec. 31, 1998

Related U.S. Application Data

[63] Continuation-in-part of application No. 09/138,636, Aug. 24, 1998, and a continuation-in-part of application No. 09/063,109, Apr. 20, 1998.

[51] Int. Cl.[7] .......................................................... A61B 8/00
[52] U.S. Cl. ........................................... 600/447; 600/458
[58] Field of Search ..................................... 600/443, 447, 600/442, 448, 444, 453, 454, 455, 458; 128/916; 73/602, 626; 382/128

[56] References Cited

U.S. PATENT DOCUMENTS

| | | | |
|---|---|---|---|
| 5,014,712 | 5/1991 | O'Donnell et al. | 600/447 |
| 5,632,277 | 5/1997 | Chapman et al. | 128/660.07 |
| 5,706,819 | 1/1998 | Hwang et al. | 128/662.02 |
| 5,844,139 | 12/1998 | Miller et al. | 73/602 |
| 5,902,241 | 5/1999 | Seyed-Bolorforosh et al. | 600/443 |
| 5,961,463 | 10/1999 | Rhyne et al. | 600/458 |
| 5,964,706 | 10/1999 | Mo et al. | 600/443 |
| 5,980,459 | 11/1999 | Chiao et al. | 600/447 |
| 6,010,456 | 1/2000 | Rhyne | 600/447 |

OTHER PUBLICATIONS

Frank, "Polyphase Complementary Codes", IEEE Trans. Inform. Theory, vol. IT–26, No. 6, Nov. 1980, pp. 641–647.

Sivaswamy, "Multiphase Complementary Codes", IEEE Trans. Inform. Theory, vol. IT–24, No. 5, Sep. 1978, pp. 546–552.

Tseng, "Complementary Sets of Sequences," IEEE Trans. Inform. Theory, vol. IT–18, No. 5, Sep. 1972, pp. 644–652.

Golay, "Complementary Series," IRE Trans. Inform. Theory, April 1961, pp. 82–87.

Lee et al., "High–Speed Digital Golay Code Flaw Detection System," Proc. 1981 Ultrasonics Symp., pp. 888–891.

Hayward et al., "A Digital Hardware Correlation System for Fast Ultrasonic Data Acquisition in Peak Power Limited Applications," IEEE Trans. Ultrason. Ferroelec. Freq. Cont., vol. 35, No. 6, Nov. 1988, pp. 800–808.

Mayer et al., "Three–Dimensional Imaging System Based on Fourier Transform Synthetic Aperture Focusing Technique," Ultrasonics, vol. 28, Jul. 1990, pp. 241–255.

Takeuchi, "An Investigation of a Spread Energy Method for Medical Ultrasound Systems. II. Proposed System and Possible Problems," Ultrasonic, vol. 17, Sep. 1979, pp. 219–224.

O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for imaging the nonlinear components of an ultrasound signal returned from ultrasound scatterers in tissue or contrast agents in blood. The method employs a code-modulated wavelet for transmission combined with correlation filtering on reception. Coding methods are used to simultaneously manipulate the linear and nonlinear terms. The manipulations affect the magnitude and temporal arrangement of the resulting decoded waveforms. Among the simultaneous manipulations of linear and harmonic decoded signals are: orthogonal linear terms, finite linear terms, minimum sidelobe with optimal peak harmonic terms and optimally compressed harmonic terms.

33 Claims, 2 Drawing Sheets

METHOD AND APPARATUS FOR HARMONIC TISSUE IMAGING AND CONTRAST IMAGING USING CODED TRANSMISSION

RELATED PATENT APPLICATIONS

This application is a continuation-in-part application of U.S. patent application Ser. No. 09/138,636 filed on Aug. 24, 1998 and is a continuation-in-part application of U.S. patent application Ser. No. 09/063,109 filed on Apr. 20, 1998.

FIELD OF THE INVENTION

This invention generally relates to ultrasound imaging of the human anatomy for the purpose of medical diagnosis. In particular, the invention relates to methods and apparatus for imaging ultrasound echo components arising from nonlinear propagation and scattering in tissue or contrast agents in blood.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The frequency shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed.

Conventional ultrasound transducers transmit a broadband signal centered at a fundamental frequency $f_0$, which is applied separately to each transducer element making up the transmit aperture by a respective pulser. The pulsers are activated with time delays that produce the desired focusing of the transmit beam at a particular transmit focal position. As the transmit beam propagates through tissue, echoes are created when the ultrasound wave is scattered or reflected off of the boundaries between regions of different density. The transducer array is used to transduce these ultrasound echoes into electrical signals, which are processed to produce an image of the tissue. These ultrasound images are formed from a combination of fundamental (linear) and harmonic (nonlinear) signal components, the latter of which are generated in nonlinear media such as tissue or a blood stream containing contrast agents. With scattering of linear signals, the received signal is a time-shifted, amplitude-scaled version of the transmitted signal. This is not true for acoustic media which scatter nonlinear ultrasound waves.

The echoes from a high-level signal transmission will contain both linear and nonlinear signal components. There are a number of classical acoustic phenomena that are either non-reciprocal or nonlinear. In the non-reciprocal category are phenomena such as: mode conversions from compression waves to shear waves, mode conversion to harmonic motions, total internal reflection along boundaries (exceeding Bruster's angle), and simple refractive bending of ray paths, plus other similar phenomena. In the nonlinear category are a great many things. The generation of second harmonics by free bubbles is well documented, as indicated above. Many components of the media should become nonlinear as the wave intensity is increased to the point that the molecular "spring constants" begin to exceed their linear or small signal range. Any nonlinearity in the media should cause a very rich form of harmonic generation, and not just the second harmonic variety. In the theory of nonlinear circuits, the signals are expressed as an infinite sum of signal components. The first term in this sum is the linear term and the higher-order terms represent signals whose spectra are multiple convolutions (in frequency) of the original spectrum. This means that much more spectral energy than only the second harmonic is created. These extra spectral components can be all over the original band as well as out of the band.

In certain instances ultrasound images may be improved by suppressing the fundamental and emphasizing the harmonic (nonlinear) signal components. If the transmitted center frequency is at $f_0$, then tissue/contrast nonlinearities will generate harmonics at $f_0$ and subharmonics at $f_0/k$, where k is an integer greater than or equal to 2. [The term "(sub)harmonic" will be used herein to refer to harmonic and/or sub-harmonic signal components.] Imaging of harmonic signals has been performed by transmitting a narrowband signal at frequency $f_0$ and receiving at a band centered at frequency $2f_0$ (second harmonic) followed by receive signal processing.

A nonlinear imaging system using phase inversion subtraction is disclosed in U.S. Pat. No. 5,632,277 to Chapman et al. First and second ultrasound pulses are transmitted into the specimen being imaged in sequence and the resulting receive signals are summed. The first and second pulses differ in phase by 180°. If the ultrasound waves undergo nonlinear propagation or nonlinear interaction with contrast agents or other nonlinear scattering media, then the returned signal will have both linear and nonlinear components. Upon summation, the linear components will cancel, leaving only the nonlinear components to be imaged. U.S. Pat. No. 5,706,819 presents an almost identical method for canceling the linear term while combining the nonlinear terms. In both patents the context of the invention is to take a single short "pulse" and alter its polarity from the first transmission to the second transmission. The two subsequent echoes are added to form an image of the nonlinear media. Applying the terminology used herein, these prior art operations may be interpreted as applying an N=1 code (where N represents the length of the code) to a single broadband "pulse". Neither patent considers the approach of creating an extended transmission by convolving wavelets (having certain desirable spectral properties) with a code, and designing that code to simultaneously affect the decoded linear term and the (sub)harmonic term.

SUMMARY OF THE INVENTION

The present invention is a method and an apparatus for imaging the nonlinear components of an ultrasound signal returned from ultrasound scatterers in tissue or contrast agents in blood. The method employs a code-modulated wavelet for transmission combined with filtering and decoding on reception. As used herein, the term "wavelet" includes arbitrary analog signals not having discrete times and amplitudes as well as pulse sequences having discrete times and amplitudes. The coding methods of the invention are used to simultaneously manipulate the linear and nonlinear terms. The manipulations affect the magnitude and temporal arrangement of the resulting decoded waveforms. Among the simultaneous manipulations of linear and harmonic decoded signals presented are: orthogonal linear terms, finite linear terms, minimum sidelobe with optimal peak harmonic terms and optimally compressed harmonic terms. All these results are achieved with codes that use lengthy (typical length N=4) transmissions comprising convolutions of a transmit code with some band-limited wavelet.

The methods of the invention always produce extended waveforms which are manipulated by means of coding to produce pulse compression and code gain for (sub)harmonic signal components, while simultaneously nulling or significantly reducing the magnitude of the interfering linear signal term. In short, the codes simultaneously manipulate the decoded linear and (sub)harmonic echoes. Most importantly, the (sub)harmonic decoded signals are made to "pulse compress" in range resolution while at the same time magnitude enhance, to improve both resolution and detection.

Considering the use of codes for harmonic imaging, three strategies are used. The most desirable strategy is to have the linear term of the signal cancel and the harmonic term spatially compress and increase its magnitude to the full gain of the code. A second strategy achieves full spatial compression and magnitude gain of the harmonic signal using the code gain, but has some residual linear component. A third strategy produces a cancellation of the linear component, and has a harmonic term with sidelobes, which degrade spatial resolution. The last strategy also produces a code gain that is equal to or less than the full code gain.

The method of the invention comprises the use of special codes to simultaneously design the linear and harmonic terms of a signaling scheme. The linear and harmonic terms can be manipulated individually to achieve several desired design objectives. Examples of design objectives are: to reduce the interference from the linear term, to enhance the detectability of the harmonic term and to improve the spatial resolution of the harmonic term. These design objectives may be mixed in various ways to achieve system performance.

The method of the invention further comprises applying codes to generate extended waveforms, the applied codes having properties which reduce, or eliminate, the linear decoded echo signal and simultaneously improve the range resolution and detection magnitude of the (sub)harmonic decoded echo signals.

Furthermore, these signaling methods, besides providing improved detection, make optimal use of the lifetime of free gas bubbles that arise from breaking the shells of contrast agents. Similarly, the enhanced magnitude of the harmonic terms implies that improved detection is achieved for a given quantity of contrast agent, allowing either improved measurement, or consistent measurement at a reduced contrast dose compared to other methods.

DETAILED DESCRIPTION OF THE PREFERRED EMBODIMENTS

Figure 1:
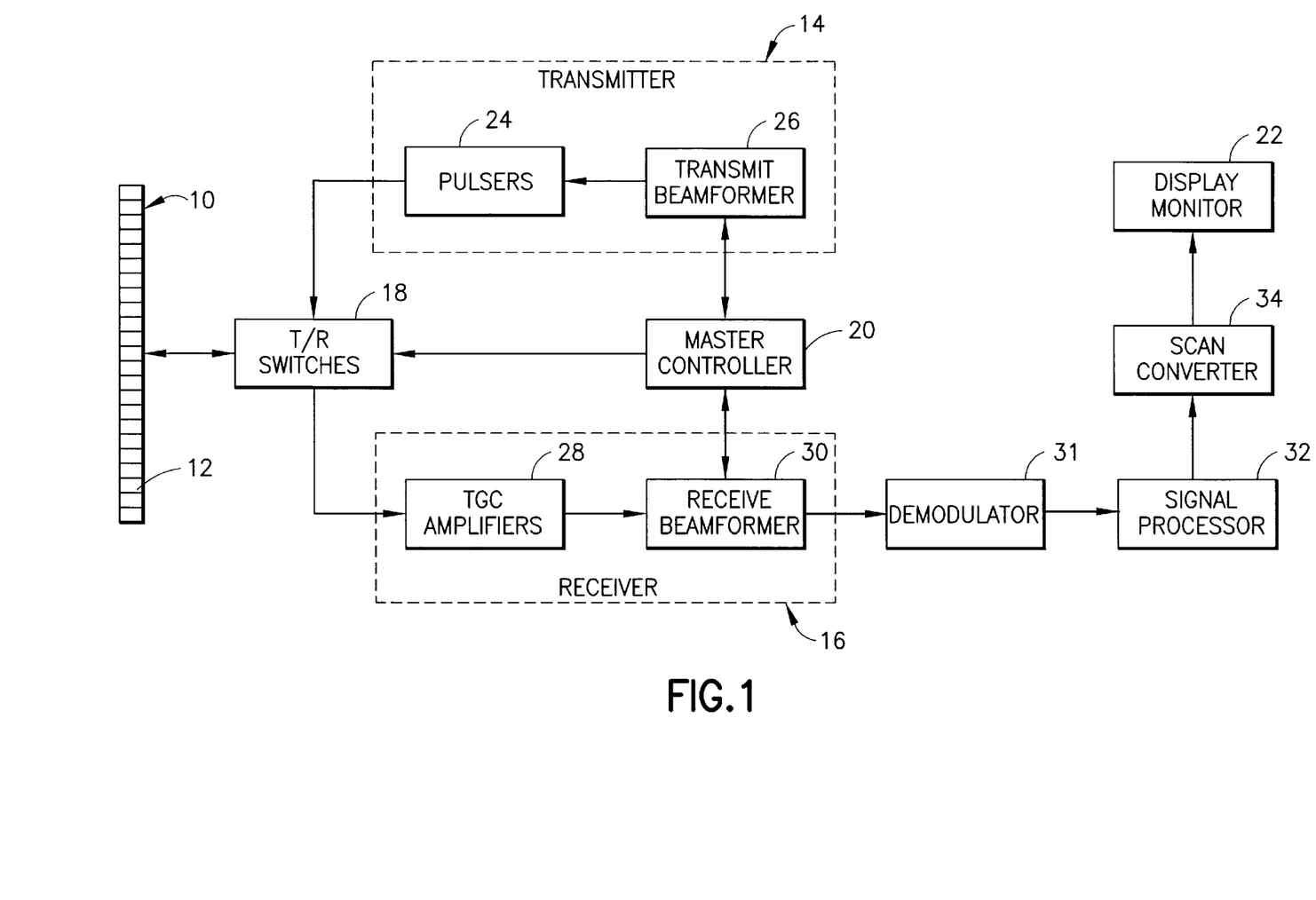
FIG. 1 is a block diagram showing an ultrasound imaging system which can be programmed to incorporate the present invention.

An ultrasonic imaging system which incorporates the present invention is depicted in FIG. 1. The system comprises a transducer array 10 consisting of a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. The receiver 16 combines the separate echo signals from each transducer element to produce a single echo signal which is used to produce a line in an image on a display monitor 22.

Under the direction of master controller 20, the transmitter 14 drives transducer array 10 such that the ultrasonic energy is transmitted as a directed focused beam. To accomplish this, respective time delays are imparted to a multiplicity of pulsers 24 by a transmit beamformer 26. The master controller 20 determines the conditions under which the acoustic pulses will be transmitted. With this information, the transmit beamformer 26 will determine the timing and the amplitudes of each of the transmit pulses to be generated by pulsers 24. The amplitudes of each transmit pulse are generated by an apodization generation circuit (not shown). The pulsers 24 in turn send the transmit pulses to each of the elements 12 of the transducer array 10 via the T/R switches 18. By appropriately adjusting the transmit focus time delays and the apodization weightings in a conventional manner, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the magnitude of the echo signal at a particular point in time represents the amount of reflection occurring at a specific range. Due to the differences in the propagation paths between a reflecting point and each transducer element 12, the echo signals will not be detected simultaneously and their amplitudes will not be equal. Gain adjustment in the axial direction, known as "time gain compensation" (TGC), is carried out by increasing or decreasing gain as a function of depth. Receiver 16 amplifies the separate echo signals via a respective TGC amplifier 28 in each receive channel. The amount of amplification provided by the TGC amplifiers is controlled through a control line (not shown). The amplified echo signals are then fed to the receive beamformer 30. Each receiver channel of the receive beamformer is connected to a respective transducer element 12 by a respective TGC amplifier 28.

Under the direction of master controller 20, the receive beamformer 30 tracks the direction of the transmitted beam, sampling the echo signals at a succession of ranges along each beam. The receive beamformer 30 imparts the proper time delays and receive apodization weightings to each amplified echo signal and sums them to provide an echo signal which accurately indicates the total ultrasonic energy reflected from a point located at a particular range along one ultrasonic beam. The receive focus time delays are computed in real-time using specialized hardware or are read from a look-up table. The receive channels also have circuitry for filtering the received pulses. The time-delayed receive signals are then summed.

In one conventional system, the frequency of the beamformer output is shifted to baseband by a demodulator 31. One way of achieving this is to multiply the input signal by a complex sinusoidal $e^{i2\pi f_0 I}$, where $f_d$ is the frequency shift required to bring the signal spectrum to baseband. The beamsummed and demodulated signal is then output to a signal processor 32. The signal processor 32 converts the summed receive signals to display data. In the B-mode (gray-scale), this would be the envelope of the signal with some additional processing, such as edge enhancement and logarithmic compression. The scan converter 34 receives the display data from signal processor 32 and converts the data into the desired image for display. In particular, the scan converter 34 converts the acoustic image data from polar coordinate (R–θ) sector format or Cartesian coordinate linear array to appropriately scaled Cartesian coordinate display pixel data at the video rate. This scan-converted acoustic data is then output for display on display monitor 22, which images the time-varying amplitude of the envelope of the B-mode signal as a gray scale. A respective scan line is displayed for each transmit beam.

In another conventional system, the RF signals are summed, equalized and envelope detected without intervening demodulation to baseband. To depict such a system, it is only necessary to remove block 31 from FIG. 1 and connect the output of the receive beamformer 30 to the input of the signal processor 32. It should be appreciated that the invention can be employed in both RF and baseband systems.

Figure 2:
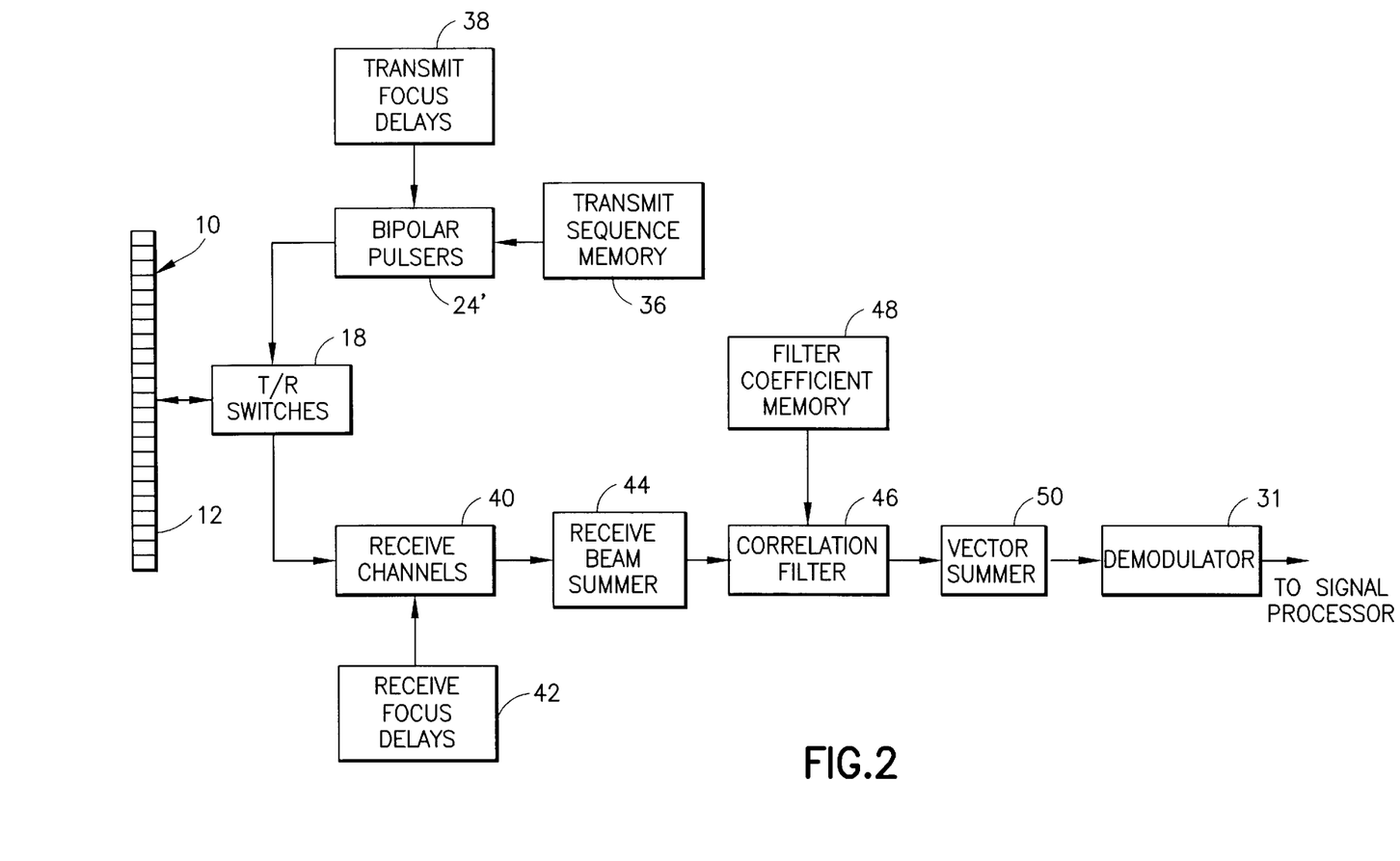
FIG. 2 is a block diagram showing an ultrasound imaging system in accordance with the invention.

FIG. 2 shows an ultrasound flow imaging system in accordance with the present invention. In this system each transducer element in the transmit aperture is pulsed using a coded sequence of a base wavelet, each pulse in the sequence being commonly referred to as a chip. The base wavelet is phase encoded, using N-digit transmit codes, to create N-chip coded wavelets which are stored in transmit sequence memory 36. Each coded wavelet read out of transmit sequence memory 36 controls activation of a multiplicity of bipolar pulsers 24' during a respective transmit firing. For example, the transducer elements are pulsed in accordance with a first coded wavelet during a first transmit firing focused at a desired transmit focal position and in accordance with a second coded wavelet during a second transmit firing focused at the same transmit focal position. The first and second coded wavelets are generated by respectively convolving first and second transmit codes with the base wavelet, i.e., by phase encoding the base wavelet using the transmit codes.

The bipolar pulsers 24' drive the elements 12 of transducer array 10 such that the ultrasonic energy produced is focused in a beam for each transmit firing. To accomplish this, transmit focus time delays from memory 38 are imparted to the respective pulsed waveforms output by the pulsers. By appropriately adjusting the transmit focus time delays in a conventional manner, the ultrasonic beams can be focused at a multiplicity of transmit focal positions to effect a scan in an image plane.

For each transmit, the echo signals from the transducer elements 12 are fed to respective receive channels 40 of the receive beamformer. Each receive channel has an analog-to-digital converter. Under the direction of the master controller (item 20 in FIG. 1), the receive beamformer tracks the direction of the transmitted beam. The receive beamformer memory 42 imparts the proper receive focus time delays to the received echo signal and sums them to provide an echo signal which accurately indicates the total ultrasonic energy reflected from a particular transmit focal position. The time-delayed receive signals are summed in receive summer 44 for each transmit firing.

The summed receive signals from successive firings are output to a correlation filter 46, which correlates the first summed receive signal with the first receive code for the first transmit firing and the second summed receive signal with the second receive code for the second transmit firing. The filtered signals derived from the first and second transmit firings focused at the same transmit focal position are summed in vector summer 50 and the summed filtered signals are then demodulated and output to the signal processor.

In accordance with the preferred embodiment of the invention, the correlation filter 46 comprises an FIR filter having N filter taps for receiving a set of N filter coefficients from a filter coefficient memory 48, where N is the number of digits of the orthogonal code. For each transmit firing, the filter coefficients $c_0, c_1, \ldots, c_{N-1}$ have scalar values equal to the respective digits of the respective receive code. The filter coefficients, like the transmit and receive time delays and the transmit codes, can be supplied by the master controller.

Filter 46 outputs the filtered signals to vector summer 50, which sums them to substantially cancel the linear component. The vector summed signal is demodulated by demodulator 31. The demodulator outputs are sent to the signal processor 32. In the B mode, signal processing includes envelope detection, edge enhancement and logarithmic compression. Following signal processing and scan conversion of each vector of data, a respective scan line is displayed on the display monitor (22 in FIG. 1).

In accordance with the invention, a nonlinear signal component is imaged by isolating the nonlinear signal component from a pair of echo signals derived from respective coded transmit firings of a base waveform having a fundamental frequency $f_0$ convolved with first and second transmit codes respectively. In the first case, the linear signal component is canceled, and the harmonic signal component is spatially compressed and undergoes an increase in magnitude to the full gain of the transmit code. In the second case, full spatial compression and magnitude gain of the harmonic signal are achieved using the code gain, but with some residual linear component. The third case produces a cancellation of the linear component, and has a harmonic term with sidelobes and a code gain that is equal to or less than the full code gain.

In accordance with another preferred embodiment of the invention, the nonlinear signals are demodulated before correlation filtering. The demodulator transforms the RF signals into their I/Q components. In this case, each baseband component will preferably be filtered by respective correlation filters. The correlation FIR filters can be implemented in software or hardware. For the case when the demodulator shifts by discrete frequencies $f_d=k/2t_b$, where k is any positive integer and $t_b$ is the duration of the transmit base waveform, the sinusoidal becomes real and the same set of filter coefficients are input to both correlation filters for the I and Q components, which thus form a real filter. In the cases when $f_d \neq k/2t_b$, the I and Q correlation filters receive different sets of filter coefficients and thus form a complex filter.

The harmonics that are generated during nonlinear propagation in tissue can be approximated as a Taylor series of functions of the transmitted signal g(t), as in this expression for a received echo:

$$r(t) = \sum_k a_k g^k(t) = \sum_k s_k(t) \qquad (1)$$

The term in the series that has the strongest second harmonic spectrum is the k=2 term. So one can analyze the performance of the harmonic imaging codes of the invention using the relationship of the linear term, k=1, to the square term, k=2. Similarly, a subharmonic term consists of k=½.

In medical ultrasound imaging the transmitted signal is typically a wavelet of compact support that is generated by a transmitter, driven through the transducer, propagated in the media and then filtered a second time by the transducer on reception. Since ultrasonic transducers function as bandpass filters, the received wavelet s(t), with spectrum S(ω), is concentrated in a band which is centered on frequency $\omega_0$ (radians per second), and may be expressed as a bandpass signal, consisting of a carrier multiplied by envelopes, $s_c(t)$ and $s_s(t)$ as in:

$$s(t) = s_c(t) \cos(\omega_0 t) - s_s(t) \sin(\omega_0 t) \qquad (2)$$

There is a well-known complex representation for bandpass signals, where the signal s(t) is related to its complex envelope, as in:

$$s(t) = \text{Re}[\tilde{s}(t) e^{j\omega_0 t}] \qquad (3)$$

In this form, the signal s(t) is the real part of the complex envelope s/tilde multiplied by a complex carrier. The complex envelope has a real part equal to $s_c(t)$ and an imaginary part equal to $s_s(t)$.

Linear filtering and coding are represented by convolving waveforms. The convolution of two bandpass signals s(t) and k(t) to produce r(t), is defined as:

$$r(t) = \int_{-\infty}^{+\infty} s(t-\sigma) k(\sigma) d\sigma = \text{Re}\left[\int_{-\infty}^{+\infty} \frac{1}{2} \tilde{s}(t-\sigma) \tilde{k}(\sigma) d\sigma e^{j\omega_0 t}\right] \qquad (4)$$

The standard definition of convolution for the waveforms s(t) and k(t), on the left of the expression, is known to be related to the convolution of their complex envelopes by a factor of ½ and the relationship in Eq. (3).

Code vectors may be represented as complex time functions, which consist of Dirac delta functions which are spaced apart in time by the code interval T. The magnitude of each successive delta function is equal to the successive element of the code vector. The time function for code vector a is given as:

$$\tilde{a}(t) \equiv \sum_{k=0}^{N-1} \delta(t - kT) a_k \qquad (5)$$

In the simplest embodiment the wavelet is a carrier wave multiplied by some envelope of finite duration, such as a rectangular function. In this case the complex envelope is a rectangular function of time, which is pure real for a cosine carrier or pure imaginary for a sine carrier. Usually, the duration of the envelope is made equal to several half cycles of the carrier. In general, the complex envelope represents the wavelet.

Using this method of analysis, the time function of the transmitted code may be convolved with the base transmission wavelet to produce the signal used in the transmitter. Similarly, any waveform in the system may be obtained by convolving the appropriate wavelet with the appropriate code time function.

As discussed above, the actual waveforms that are transmitted consist of the code vectors which have N elements. Each of the elements is a complex value of unity magnitude and some phase. The code vectors represent a time function consisting of unit impulse functions (Dirac delta functions), which are spaced apart in time by the code interval T and whose phase is identical with the associated element of the code vector. The actual signals can be constructed by convolving the base wavelet with a code time function.

The conventional notation is that N is the length of the code. As note above, the transmissions give rise to both linear and nonlinear echoes from the media. It is convenient to use linear superposition to separate the code vectors a and c from the wavelet, and represent the code operations in matrix form as shown in Eq. (6) for the transmitted and linear receive signals and in Eq. (7) for the harmonic receive signal:

$$\begin{bmatrix} a \\ c \end{bmatrix} \otimes \begin{bmatrix} b \\ d \end{bmatrix} \equiv \begin{bmatrix} a \otimes b \\ + \\ c \otimes d \end{bmatrix} = f \qquad (6)$$

$$\begin{bmatrix} A \\ C \end{bmatrix} \otimes \begin{bmatrix} b \\ d \end{bmatrix} \equiv \begin{bmatrix} A \otimes b \\ + \\ C \otimes d \end{bmatrix} = h \qquad (7)$$

In Eq. (6), both the transmitted signals and the linear received echoes are represented by the code vectors a and c in the first matrix. These code vectors are convolved with the decode vectors b and d, also of length N, in the second matrix. The results of the two convolutions are summed to form the final linear decode vector f, which is of length 2N−1. By using superposition, the linear decoded signal may be obtained by convolving the time function corresponding to vector f with the received signal wavelet $s_1(t)$, which is the base wavelet after various filtering by the transducer, medium, beamformer, etc.

In the same manner, reception of the nonlinear harmonic echoes is represented in Eq. (7) by the vectors A and C. These are convolved with the same decode vectors as in the linear case, b and d. Again the results are summed for the receptions and the harmonic decode vector h is formed, which is also of length 2N−1. As previously indicated, the decoded harmonic signal may be formed by convolving the time function of vector h with the square term of the received wavelet signal, $s_2(t)$. The matrix form used in Eqs. (6) and (7) can be easily expanded to more than two transmissions by adding row vectors.

If one transmits code vectors a and c convolved with the base wavelet, then the nonlinear or harmonic echo term can be predicted. Using the signal series given in Eq. (1), the nonlinear second harmonic signal elements will be equal to the square of the transmitted code element times the square of the wavelet. The relationship of the codes between the linear received echo and nonlinear received echo are given as:

$$\begin{bmatrix} A \\ C \end{bmatrix} \equiv \begin{bmatrix} a^2 \\ c^2 \end{bmatrix} \qquad (8)$$

Here, the signal vectors have complex-valued elements, of unity magnitude. The square implies that each code element within the vectors is individually squared. Since, each code element is a complex value of unity magnitude, the squaring process doubles the phase of the code element.

If one transmits code vectors a and c convolved with the base wavelet, then the nonlinear subharmonic echo term can also be predicted using the signal series of Eq. (1). The nonlinear subharmonic signal elements will have carrier phases that are the square root of the transmitted wave. The relationship of the codes between the linear received echo and nonlinear received echo are given as:

$$\begin{bmatrix} A \\ C \end{bmatrix} \equiv \begin{bmatrix} a^{1/2} \\ c^{1/2} \end{bmatrix} \quad (9)$$

Here, the signal vectors have complex-valued elements, of unity magnitude. The square root implies that each code element within the vectors is individually computed. Since each code element is a complex value of unity magnitude, the square root process halves the phase of the code element.

Using this notation, a number of important transformations can be defined. The first is mirror time-reversal of each transmit code and receive decode, denoted by the superscript "r", resulting in a mirror reversal of the vector's elements about the center of the vector:

$$\begin{bmatrix} a^r \\ c^r \end{bmatrix} \otimes \begin{bmatrix} b^r \\ d^r \end{bmatrix} \equiv f^r \quad (10)$$

$$\begin{bmatrix} A^r \\ C^r \end{bmatrix} \otimes \begin{bmatrix} b^r \\ d^r \end{bmatrix} \equiv h^r \quad (11)$$

Time reversal of the order of transmission has no effect on the results:

$$\begin{bmatrix} c \\ a \end{bmatrix} \otimes \begin{bmatrix} d \\ b \end{bmatrix} \equiv f \quad (12)$$

$$\begin{bmatrix} C \\ A \end{bmatrix} \otimes \begin{bmatrix} d \\ b \end{bmatrix} \equiv h \quad (13)$$

Finally, there are a number of ways to phase rotate elements of the transmit and receive matrices. The simplest is an independent rotation of the transmit matrix by x and the receive decode matrix by y as given in:

$$\begin{bmatrix} a \\ c \end{bmatrix} x \otimes \begin{bmatrix} b \\ d \end{bmatrix} y \equiv fxy \quad (14)$$

$$\begin{bmatrix} A \\ C \end{bmatrix} x^2 \otimes \begin{bmatrix} b \\ d \end{bmatrix} y \equiv hx^2 y \quad (15)$$

The values of y and x may be chosen to provide arbitrary phase rotations. For a polyphase code of modulo M, there are M possible phase rotations. Rotation by x in the linear term causes a rotation by $x^2$ in the harmonic term. Each of the transformations in Eqs. (10)–(15) can be applied simultaneously to both the fundamental and the harmonic of a paired set of codes. They will produce convolution results whose magnitudes are identical (with the exception of the mirror reversal).

There are two additional transformations, using w and z. Each of the two variables are chosen to have unity magnitude and a distinct phase of modulo M. The transformation is given by:

$$\begin{bmatrix} a_0 z^0 & a_1 z^1 & \dots \\ c_0 w z^0 & c_1 w z^1 & \dots \end{bmatrix} \otimes \begin{bmatrix} b_0 z^0 & b_1 z^1 & \dots \\ d_0 w^{-1} z^0 & d_1 w^{-1} z^1 & \dots \end{bmatrix} \equiv \quad (16)$$

$$(f_0 z^0 + f_1 z^1 + \dots + f_{2N-2} z^{2N-2})$$

The effect of the variable w is canceled completely during the convolution. The effect of the variable z is to rotate the resulting vector f, but the variable z has no effect on the magnitude of the elements of f. These two transforms cannot be applied simultaneously to both the fundamental and the harmonic because they operate jointly on the transmit and decode matrices. However, they are important in methods of synthesis where they are applied to either the fundamental or harmonic codes individually.

In accordance with the invention, there is a simple method of synthesizing arbitrary-length orthogonal codes by concatenating smaller-length orthogonal codes. Given an orthogonal code denoted as:

$$\begin{bmatrix} p \\ r \end{bmatrix} \otimes \begin{bmatrix} q \\ s \end{bmatrix} \equiv f = \overline{0} \quad (17)$$

where each code vector p, q, r and s are of length $N_0$, the result vector f has complex elements, each of which is zero. Then, one may construct orthogonal complementary codes of lengths that are multiples of $N_0$ by the following concatenation:

$$\left[ \begin{pmatrix} p \\ r \end{pmatrix} x_0 + \begin{pmatrix} p \\ r \end{pmatrix} x_1 + \dots \right] \otimes \left[ \begin{pmatrix} q \\ s \end{pmatrix} y_0 + \begin{pmatrix} q \\ s \end{pmatrix} y_1 + \dots \right] = \overline{0} \quad (18)$$

In this notation the summations indicate concatenations of the terms in parentheses. The final length is any integer multiple of $N_0$. The elements of each of the signal vectors in parentheses may be phase rotated by a complex unity magnitude variable denoted by the subscripted x and y values.

It is easily seen that, since the signals {p, r} are orthogonal to the signals {q, s}, then any combination of the values for $x_k$ and $y_k$ in the expression of Eq. (18) will have a zero result, and the total will be zero.

In accordance with the invention, a method of synthesis of the linear transmitted signal is developed using concatenation for the linear term while simultaneously allowing free variables for optimization of the harmonic term. The synthesis technique consists of concatenating orthogonal subcodes to produce the linear term codes for transmission, as in:

$$\left[ \begin{pmatrix} p \\ r \end{pmatrix} x_0 + \begin{pmatrix} p \\ r \end{pmatrix} x_1 + \dots \right] \otimes \quad (19)$$

$$\left[ \begin{pmatrix} q \\ s \end{pmatrix} y_0 + \begin{pmatrix} q \\ s \end{pmatrix} y_1 + \dots \right] \begin{bmatrix} a \\ c \end{bmatrix} \otimes \begin{bmatrix} b \\ d \end{bmatrix} = f = \overline{0}$$

which is in the form of the transmission code of Eq. (6). The corresponding second harmonic code is:

$$\left[ \begin{pmatrix} p^2 \\ r^2 \end{pmatrix} x_0^2 + \begin{pmatrix} p^2 \\ r^2 \end{pmatrix} x_1^2 + \dots \right] \otimes \quad (20)$$

-continued $$\left[\binom{q}{s}y_0 + \binom{q}{s}y_1 + \dots\right]\left[\begin{array}{c}A\\C\end{array}\right] \otimes \left[\begin{array}{c}b\\d\end{array}\right] = h_2$$

The square notation of the second harmonic receive vectors implies element by element, and the decode matrix is common to the linear and harmonic terms. Using the commutative property of convolution, the expression for the second harmonic decode $h_2$ can be rewritten as:

$$\binom{p^2}{r^2} \otimes x^2 \otimes \binom{q}{s}^r \otimes y = \left[\binom{p^2}{r^2} \otimes \binom{q}{s}^r\right] \otimes [x^2 \otimes y] = h_2 \quad (21)$$

Note that the superscript "r" denotes reversing the sequence of the vectors to allow the use of the conventional definition of the convolution operator. The form of Eq. (21) emphasizes the individual relationships of the orthogonal subcode vectors |p, r| and |q, s|, and the two independent vectors $x^2$ and y.

The convolution in the first bracket of Eq. (21) produces a pair of row vectors whose columns are summed [in keeping with the coding concept of Eq. (6)] to produce a single row vector. This row vector represents the subcode effect on the second harmonic. The convolution in the second bracket represents the effect of vectors x and y on the second harmonic. The last convolution in Eq. (21) is emphasized by:

$$\left[\binom{p^2}{r^2}^r \otimes \binom{q}{s}^r\right] \otimes [x^2 \otimes y] = h_{2SC} \otimes h_{2xy} = h_2 \quad (22)$$

The convolution of the subcode second harmonic vector, $h_{2SC}$, and the $x^2$ and y harmonic vectors, $h_{2xy}$, determines the resulting second harmonic correlation vector $h_2$. Typically, the subcode length is the shorter of the two, so that the length of vector $h_{2SC}$ is much shorter than $h_{2xy}$. Therefore the latter will dominate the sidelobe structure of the resulting vector, $h_2$. Conversely, the peak and sidelobes of the shorter $h_{2SC}$ will dominate the resolution and peak of $h_2$. Generally, the subcode is selected to produce a short, highly peaked $h_{2SC}$, with the ideal being a single peak and no sidelobes.

An identical analysis for the subharmonic signal, produces analogous relationships. Using the relationship of linear term to subharmonic term in Eq. (9), Eqs. (20)–(22) can be rewritten for the subharmonic case. The resulting relationship for the subharmonic decode vector $h_{0.5}$, equivalent to Eq. (22), is:

$$\left[\binom{p^{1/2}}{r^{1/2}}^r \otimes \binom{q}{s}^r\right] \otimes [x^{1/2} \otimes y] = h_{0.5SC} \otimes h_{0.5xy} = h_{0.5} \quad (23)$$

The same concepts apply. The influence of the subcode is given in $h_{0.5SC}$ and the influence of the selection of vectors x and y is given in $h_{0.5xy}$.

Since the selection of x and y have no effect on the linear orthogonal properties of the code, then they are free variables. This general synthesis method utilizes the design of vectors x and y to simultaneously optimize the harmonic correlation vector h. In general, the design objective is to construct harmonic correlation vectors which have high peak values and low sidelobe values.

For a given solution code pair for the linear and (sub) harmonic terms, there are a large number of equivalent pairs which may be produced by transformations. The transformations of Eqs. (10)–(15) may be applied directly to any pair of code solutions without altering the element magnitudes of the decode vectors h and f. This makes it possible to find equivalent code sets that may be more convenient for mechanization.

The general method of the invention uses subcodes which are orthogonal. Moreover, as shown in Eqs. (22) and (23), the harmonic performance of these subcodes is important to the sidelobes and peak values achieved in the harmonic decode vectors. This arises from the subcode harmonic correlation vector $h_{2SC}$ being convolved with the design vector $h_{2xy}$, as in Eqs. (22) and (23).

The ideal subcode is of length N=1 and modulo M=4, as given in:

$$\left[\begin{array}{c}a\\c\end{array}\right] \otimes \left[\begin{array}{c}b\\d\end{array}\right] = \left[\begin{array}{c}1\\-1\end{array}\right] \otimes \left[\begin{array}{c}1\\1\end{array}\right] = f = 0 \quad (24)$$

$$\left[\begin{array}{c}A\\C\end{array}\right] \otimes \left[\begin{array}{c}b\\d\end{array}\right] = \left[\begin{array}{c}1\\1\end{array}\right] \otimes \left[\begin{array}{c}1\\1\end{array}\right] = h_{2SC} = 2 \quad (25)$$

$$\left[\begin{array}{c}A\\C\end{array}\right] \otimes \left[\begin{array}{c}b\\d\end{array}\right] = \left[\begin{array}{c}1\\\pm j\end{array}\right] \otimes \left[\begin{array}{c}1\\1\end{array}\right] = h_{0.5SC} = 1 \pm j \quad (26)$$

The fundamental and second harmonic of the ideal subcode are shown in Eqs. (24) and (25) respectively. The fundamental is orthogonal and the second harmonic squares the −1 in the transmission vector to result in a peak gain of 2. For the subharmonic the square root of −1 is either j or −j, as indicated in Eq. (26). Here, there is a reduction of −3 dB in the gain of the subcode. Of course, for length N=1 there are no sidelobes.

A special case of the general method combines the synthesis of orthogonal linear term codes with optimization of the second harmonic term decode vector $h_2$ for minimal sidelobes and a maximum magnitude peak. Similarly, the method may be applied to the sub-harmonic term decode vector $h_{0.5}$ to optimize for sidelobe magnitude and peak value. This method consists of concatenating an orthogonal subcode, as in the general method, using $x^2$ and y vectors. For the optimization of the second harmonic term decode vector $h_2$, the $x^2$ and y vectors are associated with the elements of a code that is known to have a decode vector $h_{2xy}$ with minimum sidelobes and maximum peak magnitude. The convolution as in Eq. (22) with a suitable subcode vector $h_{2SC}$ results in a second harmonic decode vector with minimum sidelobes and maximum peak magnitude. The linear term transmit code is then constructed by forming the square root of the vector $x^2$, on an element by element basis for use as the x vector. Since, the formation of the square root is a nonunique mathematical operation, there are multiple transmit vector solutions in the synthesis.

For the optimization of the subharmonic term decode vector $h_{0.5}$, the $x^{1/2}$ and y vectors are associated with the elements of a code that is known to have a decode vector $h_{0.5xy}$ with minimum sidelobes and maximum peak magnitude. The convolution as in Eq. (23) with a suitable subcode vector $h_{0.5SC}$ results in a subharmonic decode vector with minimum sidelobes and maximum peak magnitude. The linear term transmit vector is constructed by forming the square of the vector $x^{1/2}$ on an element by element basis.

As for the general method, for a given solution code pair for the linear term and (sub)harmonic term in this case, there are a large number of equivalent pairs which may be produced by the transformations of Eqs. (10)–(15).

The special method will be demonstrated for the second harmonic case. The vectors $x^2$ and y vectors are associated with the first and second row vectors of a well-known Frank code of length N=4 and modulo M=4 given as:

$$[1\ 1\ 1\ 1] \otimes [-1\ 1\ 1\ 1] = [-1\ 0\ 1\ 4\ 1\ 0\ -1] = h_{2xy} \quad (27)$$

The $x^2$ vector is associated with the first row vector of Eq. (27) and the y vector is associated with the second row vector. The subcode selected is the N=1 code. Applying the synthesis method, the resulting second harmonic decode is given by:

$$\begin{bmatrix} 1 & 1 & 1 & -1 \\ 1 & 1 & 1 & -1 \end{bmatrix} \otimes \begin{bmatrix} -1 & 1 & 1 & 1 \\ -1 & 1 & 1 & 1 \end{bmatrix} = [-2\ 0\ 2\ 8\ 2\ 0\ -2] = h_2 \quad (28)$$

The synthesis of the linear term code is completed by taking the square root of the transmit vector of the Frank code in Eq. (27), which permits values of plus or minus one. Consequently, the elements of the linear term transmit code, when convolved with the subcode, may take on either positive or negative sign, as in:

$$\begin{bmatrix} 1 & -1 & 1 & -1 & 1 & -1 & j & -j \\ -1' & 1 & -1' & 1 & -1' & 1 & -j' & j \end{bmatrix} \otimes \begin{bmatrix} -1 & 1 & 1 & 1 \\ -1 & 1 & 1 & 1 \end{bmatrix} = \quad (29)$$

$$f = (\overline{0})$$

This is indicated in Eq. (29) by the two column vectors separated by commas. There are $2^N=16$ equivalent solutions for the linear transmit matrix in Eq. (29). The decode matrices are the same for the second harmonic and linear terms. The linear term produces an orthogonal result, while the harmonic term produces a result with a peak level of 2N and maximum sidelobes of 2. For this case this, where N=4, the peak-to-sidelobe ratio is 12 dB.

Another special case of the general method combines the synthesis of orthogonal linear term codes with zero sidelobe and maximum magnitude of the second harmonic decode vectors. This method consists of concatenating an orthogonal subcode, as in the general method, and using $x^2$ and y vectors that are known to be components of a code that produces zero sidelobes and maximal peak magnitude. Such codes are known as complementary codes and require two transmissions. Consequently, this method of synthesis requires four transmissions. For the first two transmissions the $x^2$ and y vectors are set equal to the first row vectors of the transmit matrix and of the decode matrix respectively of the complementary code. Subsequently, for the third and fourth transmissions the $x^2$ and y vectors are set equal to the second row vectors of the transmit matrix and of the decode matrix respectively of the complementary code. The resulting four transmit codes will exhibit the desired linear term orthogonality and the second harmonic will be optimally compressed. The linear term transmit matrix is constructed by forming the square root of the two $x^2$ vectors on an element by element basis. Since the operation of taking the square root has nonunique solutions, there are multiple solutions for the linear term transmit vectors.

This special method of code synthesis can also be applied to subharmonic term optimization. The synthesis proceeds by applying the vectors $x^{1/2}$ and y to the complementary code. The rest of the synthesis proceeds as in the second-harmonic case, resulting in the convolution of an ideal $h_{0.5xy}$ vector with the subcode vector $h_{0.5SC}$. The linear term transmission matrix is constructed by forming the square of the appropriate harmonic first matrix. For a N=1 subcode, the result will produce a nulled linear term decode and a subharmonic decoded term having zero sidelobes and a central peak reduced in magnitude 3 dB, in accord with Eq. (26).

Again, for a given solution code pair for the linear and (sub)harmonic terms, there are a large number of equivalent pairs which may be produced by the transformations of Eqs. (10)–(15).

As an example, a well-known Golay code of length N=4 and M=2 is given by:

$$\begin{bmatrix} -1 & 1 & 1 & 1 \\ 1 & -1 & 1 & 1 \end{bmatrix} \otimes \begin{bmatrix} 1 & 1 & 1 & -1 \\ 1 & 1 & -1 & 1 \end{bmatrix} = \quad (30)$$

$$[0\ 0\ 0\ 8\ 0\ 0\ 0] = h_{2xy}$$

We select the subcode of N=1 and M=4, which produces the second harmonic code in:

$$\begin{bmatrix} -1 & 1 & 1 & 1 \\ -1 & 1 & 1 & 1 \\ 1 & -1 & 1 & 1 \\ 1 & -1 & 1 & 1 \end{bmatrix} \otimes \begin{bmatrix} 1 & 1 & 1 & -1 \\ 1 & 1 & 1 & -1 \\ 1 & 1 & -1 & 1 \\ 1 & 1 & -1 & 1 \end{bmatrix} = \quad (31)$$

$$\begin{bmatrix} -1 & 0 & 1 & 4 & 1 & 0 & -1 \\ -1 & 0 & 1 & 4 & 1 & 0 & -1 \\ 1 & 0 & -1 & 4 & -1 & 0 & 1 \\ 1 & 0 & -1 & 4 & -1 & 0 & 1 \end{bmatrix} = [0\ 0\ 0\ 16\ 0\ 0\ 0] = h_2$$

The first matrix consists of the four transmissions, while the second matrix consists of the four decodes. The final second harmonic decode $h_2$ is shown to be a perfect compression with zero sidelobes and a peak equal to 4N. Inspection of the first two rows of the transmit and decode matrices reveals that they are exact copies of the first rows of the Golay code in Eq. (30). Similarly, the third and forth rows for the two matrices are copies of the second rows of the Golay code. These represent $x^2$ and y being associated with the Golay code's two independent transmits and decodes.

The code for the linear term that is associated with this second harmonic is given as:

$$\begin{bmatrix} j & 1 & 1 & 1 \\ -j & -1 & -1 & -1 \\ 1 & j & 1 & 1 \\ -1 & -j & -1 & -1 \end{bmatrix} \otimes \begin{bmatrix} 1 & 1 & 1 & -1 \\ 1 & 1 & 1 & -1 \\ 1 & 1 & -1 & 1 \\ 1 & 1 & -1 & 1 \end{bmatrix} = \quad (32)$$

$$\begin{bmatrix} j & 1+j & 2+j & 3-j & 1 & 0 & -1 \\ -j & -1-j & -2-j & -3+j & -1 & 0 & 1 \\ 1 & 1+j & j & 3-j & j & 0 & 1 \\ -1 & -1-j & -j & -3+j & -j & 0 & -1 \end{bmatrix} =$$

$$[0\ 0\ 0\ 0\ 0\ 0\ 0] = f$$

Inspecting the decoding matrices shows that they are both equal, as required. The transmission matrix of Eq. (32) consists of two concatenated codes, one for the first and second rows and the other for the third and fourth rows. The concatenated code of the first two rows uses the N=1 subcode and the term-by-term square root of the first row of the Golay code in Eq. (30). Similarly, the third and fourth rows are the concatenated code using the second row of the Golay code. The polarity reversal between rows 1 and 2 and rows 3 and 4 derives from the subcode. Careful inspection of the third matrix of Eq. (32) shows that the first two rows and the last two rows independently sum to zero, as expected.

The synthesis method permits that the linear term transmit matrix has more than this one solution. The first two row vectors taken together may be altered in sign for each successive pair of elements. Similarly, the third and forth row vectors may be similarly altered. This permits $2^{2N}$ equivalent solutions for the linear term transmission matrix.

A general method in accordance with one preferred embodiment of the invention consists of constructing a complementary code for the harmonic row vectors |A b| and |C d| in Eq. (7). This establishes an optimal compression and maximum gain for the (sub)harmonic decode. The linear term transmit code is determined, element by element, as the square root of the second harmonic transmit code or the square of the subharmonic transmit code. The linear term decode matrix is identical with the (sub)harmonic decode matrix. The linear term decode vector f is optimized for minimum magnitude by the selection of the complementary code and its corresponding linear term transmit code. The selection of these two codes is performed by computer algorithm searching for the selection that provides minimum f vector element magnitudes. The number of possible solutions for computer search is enhanced by several key factors. Firstly, there are a fixed number of complementary code kernels, with the sets of unique code set solutions defined by the transformations in Eqs. (10)–(15). Secondly, for second harmonic code synthesis there are multiple solutions for the linear term transmit matrix, which affords extra possibilities. Thirdly, the transformations of Eq. (16) may be applied to the (sub)harmonic transmit and decode matrices to further expand the possible solutions.

An example is given, using a Golay complementary code for the second harmonic code, as in:

$$\begin{bmatrix} 1 & 1 & 1 & -1 \\ 1 & 1 & -1 & 1 \end{bmatrix} \otimes \begin{bmatrix} -1 & 1 & 1 & 1 \\ 1 & -1 & 1 & 1 \end{bmatrix} = [0\ 0\ 0\ 8\ 0\ 0\ 0] = h_2 \quad (33)$$

where the second matrix is the decode matrix used in the linear term and the harmonic receive matrix is the square of the linear term transmit matrix. This complementary code produces zero sidelobes and a maximum peak magnitude of 2N. During a computer search for an optimal linear decode, the code set of Eq. (33) may be manipulated by the two transformations in Eq. (16) to expand the search opportunities. Also, the square root of the harmonic receive code permits $2^{2N}$ possible linear transmit matrices to search over. For this example, the computer determined that the optimal linear term code to be:

$$\begin{bmatrix} 1 & 1 & 1 & j \\ 1 & -1 & -j & -1 \end{bmatrix} \otimes \begin{bmatrix} -1 & 1 & 1 & 1 \\ 1 & -1 & 1 & 1 \end{bmatrix} = \quad (34)$$

$$[0\ 0\ 1-j\ 0\ 0\ 0\ -1+j] = f$$

This linear term decode vector f has two non-zero elements whose magnitudes are 15 dB below the magnitude of the second harmonic peak. Such a linear component can be further reduced, relative to the (sub)harmonic terms, by filtering.

For subcode length of N=2 and modulo M=4, the following kernels have been discovered:

$$\begin{bmatrix} 1 & -1 \\ 1 & 1 \end{bmatrix} \otimes \begin{bmatrix} 1 & 1 \\ -1 & 1 \end{bmatrix} = f = 0 \quad (35)$$

$$\begin{bmatrix} 1 & 1 \\ 1 & 1 \end{bmatrix} \otimes \begin{bmatrix} 1 & 1 \\ -1 & 1 \end{bmatrix} = h_{2SC} = (0\ 2\ 2) \quad (36)$$

-continued $$\begin{bmatrix} 1 & j \\ 1 & 1 \end{bmatrix} \otimes \begin{bmatrix} 1 & 1 \\ -1 & 1 \end{bmatrix} = h_{0.5SC} = (0\ 1-j\ 1+j) \quad (37)$$

$$\begin{bmatrix} 1 & -1 \\ 1 & j \end{bmatrix} \otimes \begin{bmatrix} 1 & j \\ -1 & 1 \end{bmatrix} = f = 0 \quad (38)$$

$$\begin{bmatrix} 1 & 1 \\ 1 & -1 \end{bmatrix} \otimes \begin{bmatrix} 1 & j \\ -1 & 1 \end{bmatrix} = h_{2SC} = (0\ 3+j\ -1+j) \quad (39)$$

$$\begin{bmatrix} 1 & j \\ 1 & 0.7+0.7j \end{bmatrix} \otimes \begin{bmatrix} 1 & j \\ -1 & 1 \end{bmatrix} = \quad (40)$$

$$h_{0.5SC} = (0\ 0.293+1.293j\ -0.293+0.707j)$$

$$\begin{bmatrix} 1 & -1 \\ 1 & -j \end{bmatrix} \otimes \begin{bmatrix} 1 & -j \\ -1 & 1 \end{bmatrix} = f = 0 \quad (41)$$

$$\begin{bmatrix} 1 & 1 \\ 1 & -1 \end{bmatrix} \otimes \begin{bmatrix} 1 & -j \\ -1 & 1 \end{bmatrix} = h_{2SC} = (0\ 3-j\ -1-j) \quad (42)$$

$$\begin{bmatrix} 1 & j \\ 1 & -0.7+0.7j \end{bmatrix} \otimes \begin{bmatrix} 1 & -j \\ -1 & 1 \end{bmatrix} = \quad (43)$$

$$h_{0.5SC} = (0\ 1.7-0.7j\ 0.3+0.7j)$$

These kernels are unique in that they are not constructed by concatenation of length N=1 subcodes. Each subcode is orthogonal in the linear term, and achieves a finite second harmonic decode $h_{2SC}$, as well as a finite subharmonic decode $h_{0.5SC}$. All the codes produce a finite correlation of duration 2. The second and third codes provide the greatest peak magnitudes for the second harmonic decode, and the best peak to sidelobe ratio. The various harmonic results can be adjusted by applying the transformations of Eq. (16) to the subcode kernels before computing the two harmonic decodes. However, since the harmonic decode performance is only relevant with regard to the orthogonal linear term, improving the magnitude of the harmonic decodes is less significant than improving the resolution (duration).

Codes synthesized in accordance with the foregoing method are respectively input into the transmit sequence memory and the decode filter coefficient memory of an ultrasound imaging system. The codes are designed to minimizing the linear component and optimally compress the (sub)harmonic component in the receive signals.

These synthesized codes are especially useful in contrast imaging, i.e., the imaging of harmonics returned from contrast agents injected into body fluid. Contrast agents have the unique property that they not only produce reflected signals at the frequency of the transmitted ultrasound pulses, but they also produce reflected signals at a harmonic or subharmonic of the transmit frequency. Contrast agents are introduced into the body with the intent of imaging those areas where the agents have reached. Therefore, they are useful in studying flow and perfusion.

In accordance with one preferred embodiment of the invention, the ultrasound transducer array is controlled to transmit a beam formed by ultrasound pulses having a transmit center frequency and focused at a desired sample volume containing contrast agents. In the receive mode, the echoes are formed into a beamsummed receive signal, which undergoes correlation filtering to extract a signal component centered at a multiple or submultiple of the transmit center frequency. This process is repeated for each sample volume in each one of a multiplicity of scan planes which intersect the region of interest in the object volume. After forming the desired (sub)harmonic signals, the ultrasound scanner processes the (sub)harmonic signals to acquire B-mode, velocity or power data.

The foregoing preferred embodiments have been disclosed for the purpose of illustration. Variations and modifications of the concept of the invention will be readily apparent to persons skilled in the art. Although the preferred embodiments contemplate mechanizing the codes in the most efficient manner, it is conceivable to transmit coded signals and decode the resulting receive signals in a less efficient manner. For example, the transmission of a transmit code can be spread out over two or more firings provided that the decoded signal corresponding to that transmit code is reconstituted from the respective receive signals from those firings. All such variations and modifications are intended to be encompassed by the claims set forth hereinafter.

What is claimed is:

1. A system for transmitting and receiving signals, comprising:

a signal transmitter for transmitting a first coded wavelet having a bandwidth centered at a fundamental frequency during a first transmission and a second coded wavelet having a bandwidth centered at said fundamental frequency during a second transmission, said first coded wavelet being derived by coding a base wavelet with a first transmit code of length N>1 and said second coded wavelet being derived by coding said base wavelet with a second transmit code of length N, said first and second transmit codes forming a code matrix;

a signal receiver for receiving first and second receive signals subsequent to said first and second transmissions respectively, each of said first and second receive signals having a bandwidth which encompasses said fundamental frequency and a (sub)harmonic frequency thereof;

a filter for correlating said first receive signal with a first receive code of length N to form a first filtered signal and correlating said second receive signal with a second receive code of length N to form a second filtered signal, said first and second receive codes forming a decode matrix; and means for vector summing said first and second filtered signals to produce a decoded signal, wherein said code and decode matrices are designed so that said decoded signal has a (sub)harmonic signal component with improved range resolution and detection magnitude as compared to the case when transmit codes of length N=1 and so that said decoded signal has substantially no linear signal component.

2. The system as recited in claim 1, wherein said code and decode matrices are designed to produce at the output of said filter substantially no linear decoded signal component and a (sub)harmonic decoded signal component which is spatially compressed and increased in magnitude to the full gain of the code with substantially no sidelobes.

3. The system as recited in claim 1, wherein said code and decode matrices are designed to produce at the output of said filter a residual linear decoded signal component and a (sub)harmonic decoded signal component which is spatially compressed and increased in magnitude to the full gain of the code with substantially no sidelobes.

4. The system as recited in claim 1, wherein said code and decode matrices are designed to produce at the output of said filter substantially no linear decoded signal component and a (sub)harmonic decoded signal component which is spatially compressed and increased in magnitude to less than the full gain of the code with substantially reduced sidelobes.

5. A system for nonlinear imaging of ultrasound scatterers, comprising:

an ultrasound transducer array comprising a multiplicity of transducer elements;

a transmitter coupled to said transducer array for pulsing a set of selected transducer elements which form a transmit aperture with a first coded wavelet having a bandwidth centered at a fundamental frequency during a first transmission and a second coded wavelet having a bandwidth centered at said fundamental frequency during a second transmission, said first coded wavelet being derived by coding a base wavelet with a first transmit code of length N>1 and said second coded wavelet being derived by coding said base wavelet with a second transmit code of length N, said first and second transmit codes forming a code matrix;

acquisition means coupled to said transducer array for acquiring first and second beamsummed receive signals subsequent to said first and second transmit firings respectively, each of said first and second beamsummed receive signals having a bandwidth which encompasses said fundamental frequency and a (sub) harmonic frequency thereof a filter for correlating said first beamsummed receive signal with a first receive code of length N to form a first filtered signal and correlating said second beamsummed receive signal with a second receive code of length N to form a second filtered signal, said first and second receive codes forming a decode matrix;

means for vector summing said first and second filtered signals to produce a decoded signal;

a processor programmed to form an image signal from said decoded signal; and means for displaying an image which is a function of said image signal, wherein said code and decode matrices are designed so that said decoded signal has a (sub)harmonic signal component with improved range resolution and detection magnitude as compared to the case when transmit codes of length N=1 and so that said decoded signal has substantially no linear signal component.

6. A system for transmitting and receiving signals, comprising:

a signal transmitter for transmitting first through fourth coded wavelets each having a bandwidth centered at a fundamental frequency during first through fourth transmissions respectively, said first through fourth coded wavelets being derived by coding a base wavelet with respective first through fourth transmit codes of length N>1, said first through fourth transmit codes forming a code matrix;

a signal receiver for receiving first through fourth receive signals subsequent to said first through fourth transmissions respectively, each of said first through fourth receive signals having a bandwidth which encompasses said fundamental frequency and a (sub)harmonic frequency thereof;

a filter for correlating said first through fourth receive signals with respective first through fourth receive codes of length N to form first through fourth filtered signals respectively, said first through fourth receive codes forming a decode matrix; and means for vector summing said first through fourth filtered signals to produce a decoded signal, wherein said code and decode matrices are designed so that said decoded signal has substantially no linear signal component and has an optimally compressed (sub)harmonic signal component.

7. A system for nonlinear imaging of ultrasound scatterers, comprising:

an ultrasound transducer array comprising a multiplicity of transducer elements;

a transmitter coupled to said transducer array for pulsing a set of selected transducer elements which form a transmit aperture with first through fourth coded wavelets each having a bandwidth centered at a fundamental frequency during first through fourth transmit firings respectively, said first through fourth coded wavelets being derived by coding a base wavelet with respective first through fourth transmit codes of length N>1, said first through fourth transmit codes forming a code matrix;

acquisition means coupled to said transducer array for acquiring first through fourth beamsummed receive signals subsequent to said first through fourth transmit firings respectively, each of said first through fourth beamsummed receive signals having a bandwidth which encompasses said fundamental frequency and a (sub)harmonic frequency thereof;

a filter for correlating said first through fourth receive signals with respective first through fourth receive codes of length N to form first through fourth filtered signals respectively, said first through fourth receive codes forming a decode matrix;

means for vector summing said first through fourth filtered signals to produce a decoded signal, a processor programmed to form an image signal from said decoded signal; and means for displaying an image which is a function of said image signal, wherein said code and decode matrices are designed so that said decoded signal has substantially no linear signal component and has an optimally compressed (sub)harmonic signal component.

8. A system for imaging ultrasound scatterers, comprising:

an ultrasound transducer array comprising a multiplicity of transducer elements;

a display monitor for displaying an image which is a function of an image signal;

a computer programmed to perform the following steps:

(a) driving a first set of transducer elements forming a transmit aperture in a transducer array with first and second coded wavelets each having a bandwidth centered at a fundamental frequency during respective first and second transmit firings focused at a transmit focal position, said first and second coded wavelets being derived by coding a base wavelet with respective first and second transmit codes of length N>1, said first and second transmit codes forming a code matrix;

(b) beamforming the echo signals detected by a second set of transducer elements forming a receive aperture in the transducer array to acquire first and second beamsummed receive signals subsequent to said first and second transmit firings respectively, each of said first and second beamsummed receive signals having a bandwidth which encompasses said fundamental frequency and a (sub)harmonic frequency thereof;

(c) correlating said first and second beamsummed receive signals with respective first and second receive codes of length N to form first and second filtered signals, respectively, said first and second receive codes forming a decode matrix;

(d) vector summing said first and second filtered signals to produce a decoded signal;

(e) forming an image signal from said decoded signal; and (f) displaying an image which is a function of said image signal on said display monitor, wherein said code and decode matrices are designed so that said decoded signal has a (sub)harmonic signal component with improved range resolution and detection magnitude as compared to the case when transmit codes of length N=1 and so that said decoded signal has substantially no linear signal component.

9. A system for imaging ultrasound scatterers, comprising:

an ultrasound transducer array comprising a multiplicity of transducer elements;

a display monitor for displaying an image which is a function of an image signal;

a computer programmed to perform the following steps:

(a) driving a first set of transducer elements forming a transmit aperture in a transducer array with first through fourth coded wavelets each having a bandwidth centered at a fundamental frequency during respective first through fourth transmit firings focused at a transmit focal position, said first through fourth coded wavelets being derived by coding a base wavelet with respective first through fourth transmit codes of length N>1, said first through fourth transmit codes forming a code matrix;

(b) beamforming the echo signals detected by a second set of transducer elements forming a receive aperture in the transducer array to acquire first through fourth beamsummed receive signals subsequent to said first through fourth transmit firings respectively, each of said first through fourth beamsummed receive signals having a bandwidth which encompasses said fundamental frequency and a (sub)harmonic frequency thereof;

(c) correlating said first through fourth beamsummed receive signals with respective first through fourth receive codes of length N to form first through fourth filtered signals, respectively, said first through fourth receive codes forming a decode matrix;

(d) vector summing said first through fourth filtered signals to produce a decoded signal;

(e) forming an image signal from said decoded signal; and (f) displaying an image which is a function of said image signal on said display monitor, wherein said code and decode matrices are designed so that said decoded signal has substantially no linear signal component and has an optimally compressed (sub)harmonic signal component.

10. A transmission and reception system comprising:

memory for storing a plurality of coded transmit sequences from respective convolutions of a base sequence with respective transmit codes of length N>1 of a code matrix and a plurality of sets of decode filter coefficients from respective receive codes of length N of a decode matrix;

a transmitter for transmitting respective coded wavelets generated from said respective coded transmit sequences, said coded wavelets being centered at a fundamental frequency and being transmitted in successive respective transmissions;

a receiver for receiving respective receive signals derived from the respective transmitted coded wavelets after their propagation through a scattering medium;

a filter for filtering the respective received signals using said respective decode filter coefficient sets to form respective filtered signals; and a vector summer for vector summing said filtered signals to form a decoded signal, wherein said code and decode matrices are designed so that said decoded signal has a (sub)harmonic signal component with improved range resolution and detection magnitude as compared to the case when transmit codes of length N=1 and so that said decoded signal has substantially no linear signal component.

11. The system as recited in claim 10, wherein said code and decode matrices are derivable by the following steps:

selecting first and second orthogonal subcodes;

selecting a vector $x_2$ and a vector y having the property that convolution of said vector $x_2$ and said vector y produces a vector $h_{2xy}$ having minimum sidelobes and maximum peak magnitude;

squaring said first orthogonal subcode on an element by element basis;

concatenating said squared first orthogonal subcode with said vector $x^2$ to form a harmonic term code vector;

concatenating said second orthogonal subcode with said vector y to form said decode matrix;

convolving said harmonic term code matrix with said decode matrix to form a harmonic correlation vector; and if said harmonic correlation vector satisfies a design requirement, constructing said code matrix by determining a square root of said vector $x^2$ on an element by element basis for use as a vector x and concatenating said first orthogonal subcode with said ector x.

12. The system as recited in claim 10, wherein said code and decode matrices are derivable by the following steps:

selecting first and second orthogonal subcodes;

selecting a vector $x_{1/2}$ and a vector y having the property that convolution of said vector $x_{1/2}$ and said vector y produces a vector $h_{0.5xy}$ having minimum sidelobes and maximum peak magnitude;

determining the square root of said first orthogonal subcode on an element by element basis;

concatenating said squared rooted first orthogonal subcode with said vector $x^{1/2}$ to form a subharmonic term code vector;

concatenating said second orthogonal subcode with said vector y to form said decode matrix;

convolving said subharmonic term code matrix with said decode matrix to form a subharmonic correlation vector; and if said subharmonic correlation vector satisfies a design requirement, constructing said code matrix by squaring said vector $x^{1/2}$ on an element by element basis for use as a vector x and concatenating said first orthogonal subcode with said vector x.

13. The system as recited in claim 10, wherein said code and decode matrices are derivable by the following steps:

selecting first and second orthogonal subcodes;

selecting a complementary code that produces zero sidelobes and maximal peak magnitude, said complementary code comprising first and second complementary transmit code row vectors and first and second complementary decode row vectors;

squaring said first orthogonal subcode on an element by element basis;

concatenating said squared first orthogonal subcode with said first complementary transmit code row vector to form first and second row vectors of a harmonic receive code matrix;

concatenating said squared first orthogonal subcode with said second complementary transmit code row vector to form third and fourth row vectors of said harmonic receive code matrix;

concatenating said second orthogonal subcode with said first complementary decode row vector to form first and second decode row vectors of said decode matrix;

concatenating said second orthogonal subcode with said second complementary decode row vector to form third and fourth decode row vectors of said decode matrix;

convolving said harmonic receive code matrix with said decode matrix to form a harmonic correlation vector; and if said harmonic correlation vector satisfies a design requirement, constructing first and second row vectors of said code matrix by determining a square root of said first and second row vectors respectively of said harmonic receive code matrix on an element by element basis for use as a first vector x and concatenating said first orthogonal subcode with said first vector x, and constructing third and fourth row vectors of said code matrix by determining a square root of third and fourth row vectors respectively of said harmonic receive code matrix on an element by element basis for use as a second vector x and concatenating said first orthogonal subcode with said second vector x.

14. The system as recited in claim 10, wherein said code and decode matrices are derivable by the following steps:

selecting first and second orthogonal subcodes;

selecting a complementary code that produces zero sidelobes and maximal peak magnitude, said complementary code comprising first and second complementary transmit code row vectors and first and second complementary decode row vectors;

square rooting said first orthogonal subcode on an element by element basis;

concatenating said square rooted first orthogonal subcode with said first complementary transmit code row vector to form first and second row vectors of a subharmonic receive code matrix;

concatenating said square rooted first orthogonal subcode with said second complementary transmit code row vector to form third and fourth row vectors of said subharmonic receive code matrix;

concatenating said second orthogonal subcode with said first complementary decode row vector to form first and second decode row vectors of said decode matrix;

concatenating said second orthogonal subcode with said second complementary decode row vector to form third and fourth decode row vectors of said decode matrix;

convolving said subharmonic receive code matrix with said decode matrix to form a subharmonic correlation vector; and if said subharmonic correlation vector satisfies a design requirement, constructing first and second row vectors of said code matrix by squaring said first and second row vectors respectively of said harmonic receive code matrix on an element by element basis for use as a first vector x and concatenating said first orthogonal subcode with said first vector x, and constructing third and fourth row vectors of said code matrix by squaring said third and fourth row vectors respectively of said harmonic receive code matrix on an element by element basis for use as a second vector x and concatenating said first orthogonal subcode with said second vector x.

15. The system as recited in claim 10, wherein said code and decode matrices are derivable by the following steps:

selecting first and second orthogonal subcodes;

selecting a code that produces minimum sidelobes and maximum peak magnitude, said code comprising a transmit vector and a decode vector;

square rooting said transmit vector on an element by element basis;

concatenating said first orthogonal subcode with the square root of said transmit vector to form said code matrix; and concatenating said second orthogonal subcode with said decode vector to form said decode matrix.

16. The system as recited in claim 10, wherein said code and decode matrices are derivable by the following steps:

selecting first and second orthogonal subcodes;

selecting a code that produces minimum sidelobes and maximum peak magnitude, said code comprising a transmit vector and a decode vector;

squaring said transmit vector on an element by element basis;

concatenating said first orthogonal subcode with the square of said transmit vector to form said code matrix; and concatenating said second orthogonal subcode with said decode vector to form said decode matrix.

17. The system as recited in claim 10, wherein said code and decode matrices are derivable by the following steps:

selecting first and second orthogonal subcodes;

selecting a complementary code that produces zero sidelobes and maximal peak magnitude, said complementary code comprising first and second complementary transmit code row vectors and first and second complementary decode row vectors;

square rooting said first complementary transmit code row vector on an element by element basis;

concatenating said first orthogonal subcode with the square root of said first complementary transmit code row vector to form first and second row vectors of said code matrix;

square rooting said second complementary transmit code row vector on an element by element basis;

concatenating said first orthogonal subcode with the square root of said second complementary transmit code row vector to form third and fourth row vectors of said code matrix;

concatenating said second orthogonal subcode with said first complementary decode row vector to form first and second decode row vectors of said decode matrix; and concatenating said second orthogonal subcode with said second complementary decode row vector to form third and fourth decode row vectors of said decode matrix.

18. The system as recited in claim 10, wherein said code and decode matrices are derivable by the following steps:

selecting first and second orthogonal subcodes;

selecting a complementary code that produces zero sidelobes and maximal peak magnitude, said complementary code comprising first and second complementary transmit code row vectors and first and second complementary decode row vectors;

squaring said first complementary transmit code row vector on an element by element basis;

concatenating said first orthogonal subcode with the square of said first complementary transmit code row vector to form first and second row vectors of said code matrix;

squaring said second complementary transmit code row vector on an element by element basis;

concatenating said first orthogonal subcode with the square of said second complementary transmit code row vector to form third and fourth row vectors of said code matrix;

concatenating said second orthogonal subcode with said first complementary decode row vector to form first and second decode row vectors of said decode matrix; and concatenating said second orthogonal subcode with said second complementary decode row vector to form third and fourth decode row vectors of said decode matrix.

19. The system as recited in claim 10, wherein said code and decode matrices are derivable by the following steps:

selecting a complementary code that produces zero sidelobes and maximal peak magnitude, said complementary code comprising first and second complementary transmit code row vectors and first and second complementary decode row vectors, said first and second complementary decode row vectors forming said decode matrix;

square rooting said first complementary transmit code row vector on an element by element basis to form a first row vector of said code matrix; and square rooting said second complementary transmit code row vector on an element by element basis to form a second row vector of said code matrix.

20. The system as recited in claim 10, wherein said code and decode matrices are derivable by the following steps:

selecting a complementary code that produces zero sidelobes and maximal peak magnitude, said complementary code comprising first and second complementary transmit code row vectors and first and second complementary decode row vectors, said first and second complementary decode row vectors forming said decode matrix;

squaring said first complementary transmit code row vector on an element by element basis to form a first row vector of said code matrix; and squaring said second complementary transmit code row vector on an element by element basis to form a second row vector of said code matrix.

21. The system as recited in claim 10, wherein said code and decode matrices are derivable by the following steps:

constructing a precursor code matrix and a precursor decode matrix; and transforming said precursor code matrix and said precursor decode matrix to form said code matrix and said decode matrix respectively.

22. The system as recited in claim 21, wherein said transforming step comprises the step of mirror time reversing the elements of each vector of said precursor code matrix and said precursor decode matrix.

23. The system as recited in claim 21, wherein said transforming step comprises the step of phase rotating said precursor code matrix and said precursor decode matrix.

24. The system as recited in claim 21, wherein said transforming step is given by Eq. (16).

25. A transmission and reception system comprising a transmitter programmed to transmit coded wavelets derived from respective convolutions of a base wavelet having a fundamental frequency with respective transmit codes of length N>1 of a code matrix, and a receiver programmed to filter receive signals using respective receive codes of length N of a decode matrix, said code and decode matrices having a property of canceling a fundamental frequency component in said receive signals and optimally compressing a (sub) harmonic frequency component in said receive signals.

26. A method of operating a transmission and reception system, comprising the steps of:

deriving a plurality of coded transmit sequences from respective convolutions of a base sequence with respective transmit codes of length N>1 of a code matrix;

storing said coded transmit sequences in said system;

deriving a plurality of sets of decode filter coefficients from respective receive codes of length N of a decode matrix;

storing said decode filter coefficient sets in said system;

transmitting respective coded wavelets generated from said respective coded transmit sequences, said coded wavelets being centered at a fundamental frequency and being transmitted in successive respective transmissions;

receiving respective receive signals derived from the respective transmitted coded wavelets after their propagation through a scattering medium;

filtering the respective received signals using said respective decode filter coefficient sets to form respective filtered signals; and vector summing said filtered signals to form a decoded signal, wherein said code and decode matrices are designed so that said decoded signal has a (sub)harmonic signal component with improved range resolution and detection magnitude as compared to the case when transmit codes of length N=1 and so that said decoded signal has substantially no linear signal component.

27. The method as recited in claim 26, wherein said code and decode matrices are derivable by the following steps:

constructing a precursor code matrix and a precursor decode matrix; and transforming said precursor code matrix and said precursor decode matrix to form said code matrix and said decode matrix respectively.

28. The method as recited in claim 26, wherein said code and decode matrices are derivable by the following steps:

constructing a (sub)harmonic term code matrix and a (sub)harmonic decode matrix producing a decoded signal having an optimally compressed (sub)harmonic signal component;

transforming said (sub)harmonic term code matrix and said (sub)harmonic decode matrix to form a transformed code matrix and a transformed decode matrix respectively; and deriving said code matrix from said transformed code matrix and setting said decode matrix equal to said transformed decode matrix.

29. The method as recited in claim 26, wherein said code and decode matrices are derivable by the following steps:

constructing a (sub)harmonic term code matrix and a (sub)harmonic decode matrix producing a decoded signal having an optimally compressed (sub)harmonic signal component; and deriving said code matrix from said (sub)harmonic term code matrix and setting said decode matrix equal to said (sub)harmonic decode matrix.

30. The method as recited in claim 27, wherein said transforming step comprises the step of mirror time reversing the elements of each vector of said precursor code matrix and said precursor decode matrix.

31. The method as recited in claim 27, wherein said transforming step comprises the step of phase rotating said precursor code matrix and said precursor decode matrix.

32. The method as recited in claim 27, wherein said transforming step is given by Eq. (16).

33. A system for transmitting and receiving signals, comprising:

a signal transmitter for transmitting first through M-th coded wavelets having a bandwidth centered at a fundamental frequency during first through M-th transmissions, where $M \geq 2$, said first through M-th coded wavelets being respectively derived by coding a base wavelet with transmit codes of length N>1 which form a code matrix;

a signal receiver for receiving first through M-th receive signals subsequent to said first through M-th transmissions respectively, each of said first through M-th receive signals having a bandwidth which encompasses said fundamental frequency and a (sub)harmonic frequency thereof;

a filter for correlating said first through M-th receive signals with receive codes of length N which form a decode matrix to form first through M-th filtered signals; and means for vector summing said first through M-th filtered signals to produce a decoded signal, wherein said code and decode matrices are designed so that said decoded signal has a (sub)harmonic signal component with improved range resolution and detection magnitude as compared to the case when transmit codes of length N=1 and so that said decoded signal has substantially no linear signal component.

* * * * *